(12) United States Patent
Kataoka et al.

(10) Patent No.: US 7,356,114 B2
(45) Date of Patent: Apr. 8, 2008

(54) X-RAY FLUORESCENCE SPECTROMETER

(75) Inventors: Yoshiyuki Kataoka, Takatsuki (JP);
Eiichi Furusawa, Takatsuki (JP);
Hisayuki Kohno, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 0 days.

(21) Appl. No.: 11/531,481

(22) Filed: Sep. 13, 2006

(65) Prior Publication Data
US 2007/0058776 A1 Mar. 15, 2007

(30) Foreign Application Priority Data
Sep. 14, 2005 (JP) ............................... 2005-266471

(51) Int. Cl.
*G01N 23/223* (2006.01)
(52) U.S. Cl. .............................. 378/44; 378/45; 378/50
(58) Field of Classification Search ............. 378/42–50
See application file for complete search history.

(56) References Cited

U.S. PATENT DOCUMENTS

| | | | |
|---|---|---|---|
| 2,926,257 A | | 2/1960 | Friedman |
| 4,796,284 A | * | 1/1989 | Jenkins .......................... 378/49 |
| 4,852,135 A | * | 7/1989 | Anisovich et al. ............. 378/49 |
| 5,081,658 A | | 1/1992 | Imai et al. |
| 5,113,421 A | | 5/1992 | Gignoux et al. |
| 5,187,727 A | | 2/1993 | Vogler et al. |
| 5,325,416 A | * | 6/1994 | Saito et al. .................... 378/50 |
| 5,408,512 A | * | 4/1995 | Kuwabara et al. ............. 378/45 |
| 5,579,362 A | * | 11/1996 | Matsuura et al. .............. 378/59 |
| 6,038,280 A | * | 3/2000 | Rossiger et al. ............... 378/50 |

(Continued)

FOREIGN PATENT DOCUMENTS

DE          19618744 A1     11/1997

(Continued)

OTHER PUBLICATIONS

Development of on-line Coating Analyzer of Galvannealed Steel Sheets at Fukuyama No. 2 CGL, Tanabe, et al.; No. NKK No. 135 (1991); XP008082312.

(Continued)

*Primary Examiner*—Irakli Kiknadze
(74) *Attorney, Agent, or Firm*—Sughrue Mion, PLLC

(57) ABSTRACT

An X-ray fluorescence spectrometer includes an X-ray source 7 for irradiating a sample 1 at a predetermined incident angle ø with primary X-rays 6, and a detecting device 9 for measuring an intensity of fluorescent X-rays 8 generated from the sample at a predetermined detection angle α and β, wherein with two combinations of the incident angle ø and the detection angle α and β, in which combinations the incident angles ø and/or the detection angles α and β are different from each other, each intensity of the fluorescent X-rays 8 is measured and, also, the incident angle ø and the detection angle α and β in each of the combination are so set that with respect to a measurement depth represented by the coating weight, at which the intensity of the fluorescent X-rays 8 attains a value equal to 99% of the uppermost limit when the coating weight of a target coating to be measured is increased, respective measurement depths in the two combinations may be a value greater than the coating weight of a coating 3.

3 Claims, 2 Drawing Sheets

U.S. PATENT DOCUMENTS

| | | |
|---|---|---|
| 6,118,844 A | 9/2000 | Fischer |
| 6,376,267 B1 * | 4/2002 | Noack et al. ................. 438/16 |
| 2003/0142781 A1 * | 7/2003 | Kawahara et al. ............ 378/44 |

FOREIGN PATENT DOCUMENTS

| | | |
|---|---|---|
| DE | 19739321 A1 | 3/1999 |
| EP | 0389774 | 10/1990 |
| JP | 55-024680 | 2/1980 |
| JP | 58-223047 | 12/1983 |
| JP | 60-236052 | 11/1985 |
| JP | 02-257045 | 10/1990 |
| JP | 04-232448 | 8/1992 |

OTHER PUBLICATIONS

Analysis of Coating Weight and Iron Content for Iron-Zinc Alloy coatings by Using x-ray Fluorescence with Multiple Regression; Hong and Kwon; Nov. 18, 2002; Journal of the Korean Physical Society, vol. 42, No. 2, Mar. 2003, pp. 413-417.

* cited by examiner

X-RAY FLUORESCENCE SPECTROMETER

BACKGROUND OF THE INVENTION

1. Field of the Invention

The present invention relates to an X-ray fluorescence spectrometer for analyzing the coating weight of and the composition of a coating of a galvanneal sheet steel.

2. Description of the Conventional Art

Hitherto, the technique is well known in the art, of analyzing the coating weight of and the composition of a coating of a galvanneal sheet steel through the X-ray fluorescence analysis. (See, for example, the Japanese Laid-open Patent Publications No. 58-223047, No.55-24680, No. 60-236052, No. 2-257045, and No. 4-232448.) According to those known techniques, based on the idea discussed below, the intensities of the fluorescent X-rays are measured with the use of two combinations of the angle of incidence of primary X-rays and the angle of detection of fluorescent X-rays, in which combinations the angles of incidence and/or the angles of detection are different from each other.

In general, when the coating weight of a target film to be measured is increased, the intensity of the fluorescent X-rays then obtained increases as well, but there is the uppermost limit which is referred to as the infinite thickness intensity. With respect to the target film to be measured having a certain composition, in the measurement system including an X-ray source, of which primary X-rays have a predetermined wavelength distribution, and a detecting device for detecting fluorescent X-rays of a predetermined wavelength, once the angle of incidence of the primary X-rays and the angle of detection of the fluorescent X-rays are fixed, the depth to which such measurement system can measure the target film to be measured is fixed. This measurement depth is indicated by the coating weight, at which the intensity of the fluorescent X-rays attains a value equal to 99% of the uppermost limit referred to above, that is, the infinite thickness intensity.

In view of the above, using the two measurement systems, of which measurement depths are different from each other, the coating weight of and the composition of the coating are analyzed by obtaining different information (the different intensities of the fluorescent X-rays) from different depths of the coating, but according to the conventional techniques, the angle of incidence of the primary X-rays and the angle of detection of the fluorescent X-rays are so set that with respect to the measurement system of which measurement depth is shallow, the measurement depth can be smaller than the coating weight of the coating, whereby the composition of the coating is determined by removing information from the substrate sheet steel and relying only on the intensity of the fluorescent X-rays obtained with the measurement system, of which measurement depth is shallow.

However, since the intensity of the fluorescent X-rays given by the measurement system is low as the position from which the fluorescent X-rays are emitted is deep, that is, since the measurement sensitivity of the measurement system is low with increase of the depth of the target site, the measurement system, of which the measurement depth is shallow, according to the conventional art lacks a measurement sensitivity at the substrate sheet steel and the deep position in the coating from the surface and a large difference occurs between the measurement sensitivity at a shallow (adjacent the surface) position of the coating and the measurement sensitivity at a deep position (adjacent the substrate sheet steel) of the coating. Thus, since according to the conventional techniques, the composition of the coating is determined almost based on only the intensity of the fluorescent X-rays from the shallow area of the coating, an accurate analysis is possible with, for example, an electro-galvanized Zn—Fe alloy sheet steel having a coating of a composition uniform in a direction of depth thereof, but sufficiently accurate analysis is impossible with the galvanneal sheet steel having a coating of an inhomogeneous composition in a direction of depth thereof.

SUMMARY OF THE INVENTION

The present invention has been devised in view of the problems inherent in the conventional techniques and has for it subject to provide an X-ray fluorescence spectrometer capable of accomplishing a sufficiently accurate analysis of the coating weight of and the composition of the coating on the galvanneal sheet steel, of which composition is inhomogeneous in a direction of depth thereof.

In order to accomplish the foregoing object of the present invention, there is provided an X-ray fluorescence spectrometer for analyzing the coating weight of and an in-depth average composition of a coating while a galvanneal sheet steel having the coating of an in-depth inhomogeneous composition is used as a sample, which spectrometer includes an X-ray source for irradiating the sample at a predetermined angle of incidence with primary X-rays, and detecting device for measuring an intensity of fluorescent X-rays generated from the sample at a predetermined angle of detection. And, with two combinations of the angle of incidence and the angle of detection, in which combinations the angles of incidence and/or the angles of detection are different from each other, each intensity of the fluorescent X-rays is measured. Here, the angle of incidence and the angle of detection in each of the combination are so set that with respect to a measurement depth represented by the coating weight, at which the intensity of the fluorescent X-rays attains a value equal to 99% of the uppermost limit when the coating weight of a target coating to be measured is increased, respective measurement depths in the two combinations may be a value greater than the coating weight of the coating.

According to the present invention, in each of the two combinations of the angle of incidence of the primary X-rays and the angle of detection of the fluorescent X-rays, in which combinations the angles of incidence and/or the angles of detection are different from each other, that is, in each of two measurement systems the incident angle and the detection angle are so set that the values of measurement depth are greater than the coating weight of the coating. Therefore even with the measurement system of which measurement depth is shallow, the fluorescent X-rays from a deep position of the coating are detected and the difference between the measurement sensitivity at the shallow position of the coating and the measurement sensitivity at a deep position of the coating is small as compared with that according to the conventional art. Accordingly, the coating weight of and the composition of the coating in the galvanneal sheet steel, which has the in-depth inhomogeneous composition can be analyzed sufficiently accurately.

In the present invention, the measurement depth in one of the two combinations is preferably of a value equal to or greater than 1.5 times the coating weight of the coating and the measurement depth in the other of the two combinations is preferably of a value equal to or greater than twice the measurement depth in such one of the two combinations.

Also in the present invention, the galvanneal sheet steel having one or more coating films on the coating (the galvanneal coating) may be used as the sample, and a detecting device may be provided for measuring an intensity of fluorescent X-rays generated from an element contained in the coating films; so that the coating weight of and/or the composition of the coating film can be analyzed simultaneously with the coating weight of and the average composition in the direction of depth of the coating.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Figure 1:
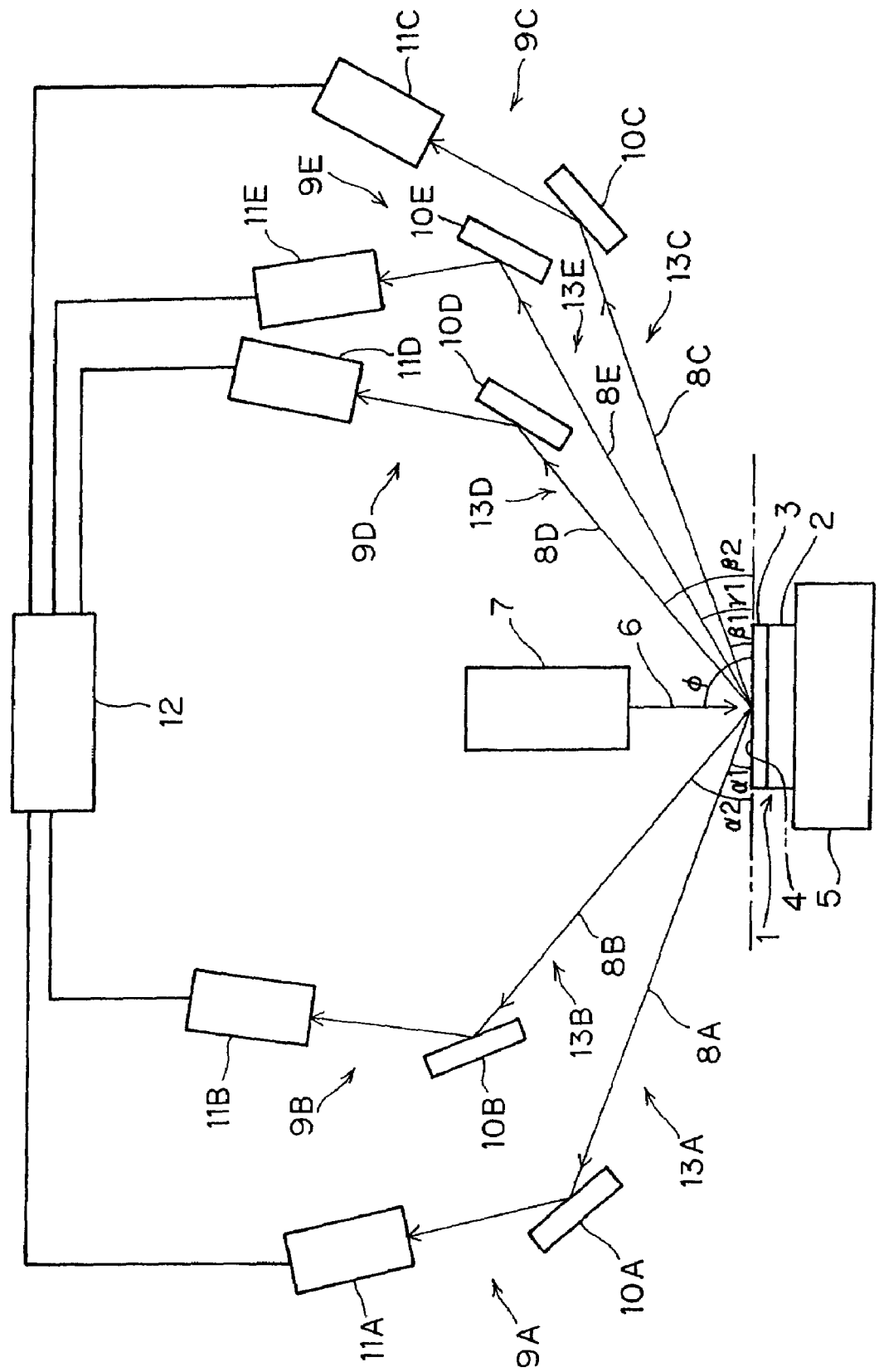
FIG. 1 is a schematic diagram showing an X-ray fluorescence spectrometer according to a preferred embodiment of the present invention.

Hereinafter, a X-ray fluorescence spectrometer according to a preferred embodiment of the present invention will be described with reference to the accompanying drawings. As shown in FIG. 1, this spectrometer is an X-ray fluorescence spectrometer operable, while a galvanneal sheet steel 1, including a substrate sheet steel 2 and a coating 3 lying on the substrate sheet steel 2 and having inhomogeneous composition in a direction depth thereof, is placed as a sample on a sample table 5, to analyze the coating weight of and an in-depth average composition of the coating 3, and which includes an X-ray source 7 such as, for example, an X-ray tube of an Rh target for irradiating the sample 1 at a predetermined incident angle ø, for example, 90° in the illustrated embodiment, with primary X-rays 6, detecting devices 7 for measuring intensities of fluorescent X-rays generated from the sample at predetermined detection angles $\alpha$ and $\beta$, and a calculating device 12 such as, for example, a computer for receiving respective outputs from the detecting devices 9 to calculate the coating weight of and the composition of the coating 3.

Each of the detecting devices 9 for detecting the fluorescent X-rays 8 of a respective predetermined wavelength includes a spectroscopic device 10, a detector 11 and a pulse height analyzer (not shown) and form a measurement system 13 together with the X-ray source 7 in the form of the previously described X-ray tube of the Rh target, in which the primary X-rays 6 have a predetermined wavelength distribution. It is to be noted that the spectroscopic device 10 and the detector 11 are mounted on each measuring device called fixed channel.

In the present invention, in a manner similar to the conventional technique discussed hereinbefore, for the analysis of the composition of and the coating weight of the coating 3, each intensity of the fluorescent X-rays is measured with the use of two combinations of the angle of incidence of primary X-rays and the angle of detection of fluorescent X-rays, in which combinations the angles of incidence and/or the angles of detection are different from each other, and, in order to accommodate this, in the spectrometer according to the illustrated embodiment, four measurement systems 13A, 13B, 13C and 13D are employed for the analysis of the composition of and the coating weight of the coating 3, while the X-ray source 7 and the angle of incidence ø (90°) of the primary X-rays are used commonly.

And, in the measurement system 13A, of which measurement depth is shallow with respect to Fe, the angle of detection $\alpha 1$ of the fluorescent X-rays 8A is set and, in the measurement system 13B, of which measurement depth is deep with respect to Fe, the angle of detection $\alpha 2$ of the fluorescent X-rays 8B is set. Similarly, in the measurement system 13C, of which measurement depth is shallow with respect to Zn, the angle of detection $\beta 1$ of the fluorescent X-rays 8C is set and, in the measurement system 13D, of which measurement depth is deep with respect to Zn, the angle of detection $\beta 2$ of the fluorescent X-rays 8D is set. Depending on the line type of the fluorescent X-rays 8 to be measured and the numerical values of the angles of detection $\alpha$ and $\beta$ will be described later. It is to be noted that in the present invention, for each element to be measured, in providing the two combinations of the angle of incidence of primary X-rays and the angle of detection of fluorescent X-rays, in which combinations at least one of the incident angles and the detection angles are different from each other, that is, in providing the two measurement systems, the incident angles and the detection angles may be different from each other or either one of the incident angles and the detection angles may be different.

Also, since in the spectrometer according to the illustrated embodiment, in order to render a galvanneal sheet steel having the coating 3, on which a coating film 4 resulting from a chromate treatment is formed, to be a sample 1 as well a detecting device 9E is provided for measuring an intensity of fluorescent X-rays 8E generated from Cr contained in the coating film 4 and, therefore, the coating weight of the coating film 4 can be analyzed simultaneously with the coating weight of and the in-depth average composition of the coating 3. For the coating film 4, what has been phosphated can be additionally enumerated.

The detecting device 9E for analyzing the coating weight of the coating film 4, too, include a spectroscopic device 10E, a detector 11E and a pulse height analyzer (not shown) so that the fluorescent X-rays 8E of a predetermined wavelength can be detected, and form a measurement system 13E together with the X-ray source 7 in the form of the previously described X-ray tube of the Rh target, in which the primary X-rays 6 have a predetermined wavelength distribution. It is to be noted that in this spectrometer, although only the coating weight deposit of the coating film is analyzed while the composition thereof is known, if the amount of deposit of and the composition of the coating film consisting of two elements are desired to be analyzed, two measurement systems will be required so that the fluorescent X-rays of respective predetermined wavelengths can be detected. In such case, two sets of the spectroscopic devices and the detectors may be mounted on measuring devices called fixed channels each for one set, or one set of the spectroscopic device and the detector may be mounted on a scanning type goniometer so that they can be drivingly associated with each other. Also, where a multi-layer coating film is to be analyzed, the measurement systems has to be increased according to the number of elements that are subject to analysis.

Figure 2A:
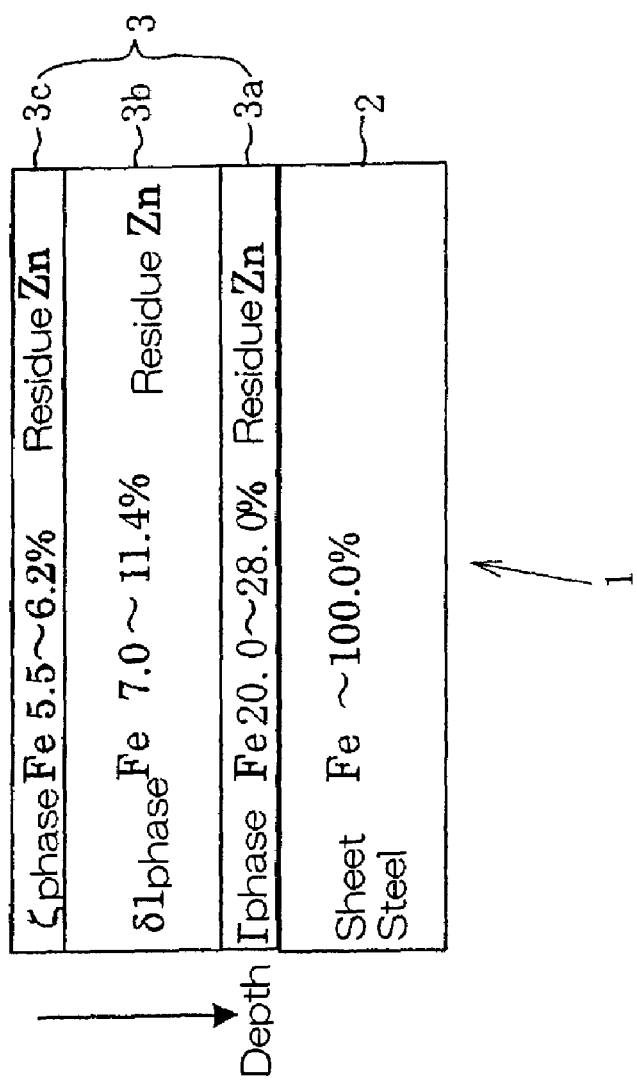
FIG. 2A is a structural diagram showing the details of a galvanneal sheet steel.

By the way, with respect to the analysis of the coating weight of and the composition of the coating 3, the line type of the fluorescent X-rays 8 to be measured and the numerical values of the detection angles α and β will now be discussed in detail hereinafter. As shown in FIG. 2A, the galvanneal sheet steel 1, which is the sample, has the coating 3 overlaid on the substrate sheet steel 2 and having a composition inhomogeneous in a direction of depth thereof. The coating 3 is divided into three phases of a Γ phase 3a, a δ1 phase 3b and a ζ phase 3c from below, each phase having a different composition. With respect to the fluorescent X-rays generated from the coating 3, the sensitivity per unit weight of the element to be measured relative to the direction of depth of the coating 3 decreases exponentially with increase of the depth.

Figure 2B:
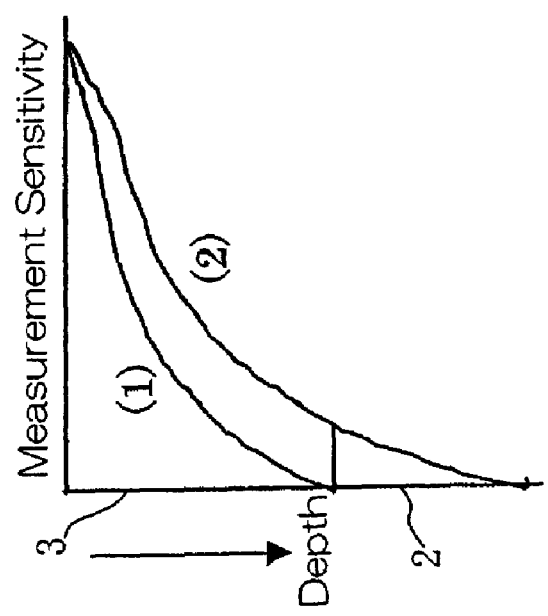
FIG. 2B is a conceptual diagram showing the manner of change of measurement sensitivity with change in depth of the coating.

A conceptual diagram showing this condition is shown in FIG. 2B, in which the curve (1) represents the relation between the depth and the measurement sensitivity where the depth of measurement is the same as the coating weight of the coating and the curve (2) represents the relation between the depth and the measurement sensitivity where the depth of measurement is larger than the coating weight of the coating. It is to be noted that, where Zn is measured, no X-rays of Zn is detected from the substrate sheet steel 2 that does not contain Zn, even in the case of the curve (2).

In the case of the curve (1), the measurement sensitivity to the fluorescent X-rays generated per unit weight of the Γ phase 3a is far lower than the respective measurement sensitivities to the fluorescent X-rays generated per unit weight of the δ1 phase and the ζ phase 3c. In contrast thereto, in the case of the curve (2), the measurement sensitivity of the Γ phase 3a is lower than the respective measurement sensitivities of the δ1 phase and the ζ phase 3c after all, but the difference between those measurement sensitivities is not so large as that in the case of the curve (1). In other words, in order to avoid the determination of the composition of the coating 3 almost based on only the intensity of the fluorescent X-rays from the δ1 phase 3b and the ζ phase 3c which are shallow side in the coating 3, of which composition is not uniform in a direction of depth thereof, large measurement depth is preferable.

In view of this, in the present invention, for each element to be measured, two combinations of the angle of incidence of primary X-rays and the angle of detection of fluorescent X-rays, in which combinations at least one of the angles of incidence and the angles of detection are different from each other, that is, in order that in the two measurement system, the values of measurement depth become larger than the coating weight of the coating and, accordingly, the measurement depth becomes larger than the coating weight of the coating even in the measurement system having the measurement depth that is shallow, the incident angle and the detection angle are determined.

The spectrometer according to this embodiment is provided, as shown in FIG. 1, with the four measurement systems 13A, 13B, 13C and 13D for the analysis of the coating weight of and the composition of the coating 3, but the X-ray source 7 and the angle of incidence ø (90°) of the primary X-rays 6 are used in common, the setting of the detection angle α1 in the measurement system 13A for the shallow measurement depth for Fe, the setting of the detection angle α2 in the measurement system 13B for the large measurement depth for Fe, the setting of the detection angle β1 in the measurement system 13C for the shallow measurement depth for Zn and the setting of the detection angle β2 in the measurement system 13D for the deep measurement depth for Zn are problematic.

In view of the above, the measurement intensities are theoretically calculated under the following conditions and analysis errors are tabulated in Table 1 and Table 2 for evaluation. As reference conditions of Tables 1 and 2, the coating weight of the coating: 46.8 g/m$^2$, the content of Fe in the coating: 11.4%, the coating weight of the Γ phase: 7.4 g/m$^2$ and the content of Fe in the Γ phase: 24.0%, the coating weight of the δ1 phase: 37.7 g/m$^2$ and the content of Fe in the δ1 phase: 9.2%, the coating weight of the ζ phase: 1.7 g/m$^2$ and the content of Fe in the ζ phase: 5.8%, α2=β2=40°, α1, β1=5, 10, 20°, the Fe measurement line: Fe–Kα, the Zn measurement line (the measurement system 13D having the deep measurement depth): Zn–Kβ, the Zn measurement line (the measurement system 13C having the shallow measurement depth): Zn–Kα.

It is to be noted that in the FP method, in which the coating weight and the composition are determined in reference to the measurement intensities, the following intensity ratios $I_H$ and $I_L$ are used. Here, the subscript Zn–Kβ(H) represents the intensity of Zn–Kβ on a deep side of the measurement depth, that is, in the measurement system on a high angle (High) side and the subscript Zn–Kα(L) represents the intensity of Zn–Kβ on a shallow side of the measurement depth, that is, in the measurement system on a low angle (Low) side.

$$I_H = I_{Zn-K\beta(H)} / I_{Fe-K\alpha(H)}$$

$$I_L = I_{Zn-K\alpha(L)} / I_{Fe-K\alpha(L)}$$

For the conditions of the Table 1, the coating weight of the Γ phase: 7.4 g/m$^2$ (the standard quantity) and the content of Fe in the Γ phase: 24.0% (the standard quantity), the coating weight of the δ1 phase: 39.4 g/m$^2$ (increased from the standard quantity by a quantity corresponding to the amount of the ζ phase subtracted) and the content of Fe in the δ1 phase: 9.05%, the coating weight of the ζ phase: 0 g/m$^2$. For the conditions of Table 2, the coating weight of the Γ phase: 3.7 g/m$^2$ (half of the standard quantity) and the content of Fe in the Γ phase: 24.0% (the standard quantity), the coating weight of the δ1 phase: 41.4 g/m$^2$ (increased from the standard quantity by a quantity corresponding to the amount of the Γ phase subtracted) and the content of Fe in the δ1 phase: 10.5%, the coating weight of the ζ phase: 1.7 g/m$^2$ (the standard quantity) and the content of Fe in the ζ phase: 5.8% (the standard quantity).

TABLE 1

When the coating weight of the ζ phase is 0
(when the coating weight is 46.8 g/m$^2$ and the content of Fe is 11.4%)

| Detection Angle on Low Angle Side | Error (g/m$^2$) in Zn—Fe Coating Weight. | Error (%) in Fe Content |
|---|---|---|
| 5° | 0.67 | 0.62 |
| 10° | 0.31 | 0.33 |
| 20° | 0.16 | 0.22 |

(The coating weight of the δ1 phase is increased by a quantity corresponding to the coating weight of the ζ phase subtracted.)

TABLE 2

When the coating weight of the Γ phase is halved
(when the coating weight is 46.8 g/m² and the content of Fe is 11.4%)

| Detection Angle on Low Angle Side | Error (g/m²) in Zn—Fe Coating Weight. | Error (%) in Fe Content |
|---|---|---|
| 5° | 0.88 | 1.28 |
| 10° | 0.79 | 1.21 |
| 20° | 0.65 | 1.09 |

(The coating weight of the δ1 phase is increased by a quantity corresponding to the coating weight of the Γ phase reduced.)

With respect to the ratio of the respective amounts of deposit of the Γ, δ1 and ζ phases, in any of the Tables 1 and 2, it will readily be seen that the analysis error is smaller with increase of the respective detection angle α1 and β1 from 5° to 10° and 20° on the measurement system which measurement depth is shallow, that is, the measurement system 13A or 13C on the low angle side.

It is to be noted that with respect to Zn, Zn–Kβ was chosen as the measurement line in place of Zn–Kα in the measurement depth which is deep, that is, in the measurement system 13D on the high angle side, in order to further increase the measurement depth. Also, the intensity ratios $I_H$ and $I_L$ were employed because there is such an effect that the difference in measurement depth on the high and low angle sides increase substantially and, when a surface of the sample move up and down and the distance to the measurement system changes during the on-line measurement, influence brought about thereby can be reduced. However, unless such an effect is desired for, the intensities, $I_{Zn-K\beta(H)}$ and $I_{Zn-K\alpha(L)}$, may be employed in place of the intensity ratios $I_H$ and $I_L$ so that the coating weight and the composition thereof can be determined with the FP method.

In the next place, the measurement depth of the measurement lines Zn–Kβ and Zn–Kα will be examined. Assuming the composition (Fe Content: 11.0%) of the coating to be uniform in a direction of depth, and the detection angles on the high and low angle sides to be β2=40° and β1=5°, 10° and 20°, each theoretical intensity of the fluorescent X-rays generated from the coating is calculated to determine the measurement depth, which is tabulated in Tables 3 and 4.

TABLE 3

Measurement Depth on High Angle Side (g/m²)

| Emission Angle on High Angle Side | Zn - Kβ |
|---|---|
| 40° | 325 |

TABLE 4

Measurement Depth on Low Angle Side (g/m²)

| Emission Angle on Low Angle Side | Zn - Kα |
|---|---|
| 5° | 50 |
| 10° | 80 |
| 20° | 159 |

As hereinbefore described, in this spectrometer, the detection angle is so set that even the measurement depth which is shallow, that is, the measurement depth with the measurement system on the low angle side is larger than the coating weight of the coating. Since the coating weight of the regular galvanneal coating is within the range of 30 to 90 g/m², the angle 40° on the high angle side in Table 3 has no problem, but only the angle 20° on the low angle side in Table 4 satisfied this condition and the measurement depth is at least 1.7 times the coating weight of the coating (159÷90≈1.77).

On the other hand, if the detection angle on the high angle side and the detection angle on the low angle side are extremely close to each other, the difference in absorption characteristic between those two measurement systems is too small and the analytical value changes considerably with a slight change of the intensity, resulting in an analysis error that is poor measuring precision during the actual measurement. In view this, the difference between the detection angle on the high angle side and the detection angle on the low angle side is preferred to be large. The measurement depth at the angle 40° on the high angle side in Table 3 is twice the measurement depth at the angle 20° on the low angle side in Table 4 (325÷15≈2.04). With this combination of the detection angles, the following sufficiently high measuring precision can be obtained. The measuring precision: 0.05 g/m² when the coating weight (Zn—Fe Coating Weight): 50 g/m². The measuring precision: 0.03% when the composition of the coating (Fe Content): 11.0%.

With respect to the measurement line Fe–Kα, since the Fe–Kα generated from the substrate sheet steel, too, is measured, the measurement depth cannot be determined in a manner similar to the measurement of Zn–Kβ and Zn–Kα described hereinabove, but since the measuring depth is simillar to that of Zn–Kα with the same detection angle, there should be no problem even if the detection angle is set to the same value as that in the measurement system for Zn.

Summarizing the foregoing, in the present invention, for each of the elements to be measured, in two combinations of the angle of incidence of the primary X-rays and the angle of detection of the fluorescent X-rays, in which combinations at least one of the angles of incidence and the angles of detection are different from each other, that is, in the two measurement system, the measurement depth in one of them is preferably equal to or greater than 1.5 times of the coating weight of the coating while the measurement depth in the other of them is preferably equal to or greater than twice the measurement depth in such one of them. With the spectrometer according to the illustrated embodiment, with respect to the element Zn to be measured, for example, in the two measurement systems 13C and 13D shown in FIG. 1, the measurement depth in the measurement system 13C is of a value at least 1.7 times of the coating weight of the coating 3 and the measurement depth in the measurement system 13D is of a value twice the measurement depth in the measurement system 13C.

As hereinbefore described, in the spectrometer according to the illustrated embodiment, the galvanneal sheet steel deposited on the coating 3 and having the coating film 4, which has been treated with chromate, is used as the sample 1 and, for the purpose of analyzing the coating weight of the coating film 4, the one detecting device 9E for measuring the intensity of the fluorescent X-rays 8E generated from the element contained in the coating film 4, that is, Cr is employed to form the associated measurement system 13E together with the X-ray source 7.

With respect to the detection angle γ1 in this measurement system 13E, since the coating film 4 formed on the coating 3 is thin as compared with the coating 3 and the element to be measured is other than Fe and Zn, the detection angle γ1 is less limited and the standard detection angle (about 20 to 45°) is sufficient. Since K lines of Fe and Zn from the coating 3 are not generally absorbed so much, it is possible to analyze the coating weight of the coating film 4 simultaneously with the coating weight of and the in-depth average composition of the coating 3.

What is claimed is:

1. An X-ray fluorescence spectrometer for analyzing a coating weight of and an in-depth average composition of a coating while a galvanneal sheet steel having the coating of an in-depth inhomogeneous composition is used as a sample, which spectrometer comprises:
   an X-ray source for irradiating the sample at a predetermined angle of incidence with primary X-rays, and
   a detecting device for measuring an intensity of fluorescent X-rays generated from the sample at a predetermined angle of detection;
   wherein with two combinations of the angle of incidence and the angle of detection, in which combinations the angles of incidence and/or the angles of detection are different from each other, each intensity of the fluorescent X-rays is measured, and
   the angle of incidence and the angle of detection in each of the combination are so set that with respect to a measurement depth represented by the coating weight, at which the intensity of the fluorescent X-rays attains a value equal to 99% of the uppermost limit when the coating weight of a target coating to be measured is increased, respective measurement depths in the two combinations is a value greater than the coating weight of the coating.

2. The X-ray fluorescence spectrometer as claimed in claim 1, wherein the measurement depth in one of the two combinations is of a value equal to or greater than 1.5 times the coating weight of the coating and the measurement depth in the other of the two combinations is of a value equal to or greater than twice the measurement depth in such one of the two combinations.

3. The X-ray fluorescence spectrometer as claimed in claim 1, wherein the galvanneal sheet steel having one or a plurality of coating films on the coating is used as the sample, and further comprising a detecting device for measuring an intensity of fluorescent X-rays generated from an element contained in the coating films; and wherein the coating weight of and/or the composition of the coating film is analyzed simultaneously with the coating weight of and the in-depth average composition of the coating.

* * * * *